United States Patent
Gruen et al.

(10) Patent No.: US 6,217,514 B1
(45) Date of Patent: Apr. 17, 2001

(54) LARYNGOSCOPE

(75) Inventors: Arthur Lawrence Gruen, Rancho Santa Fe; Erwin Caldwell Handley, Jr., Del Mar; Paul Philip Brown, San Diego, all of CA (US); Jens Ole Sorensen, Cayman Kai (KY)

(73) Assignee: Gruhan Technologies, Inc., Del Mar, CA (US)

( * ) Notice: Subject to any disclaimer, the term of this patent is extended or adjusted under 35 U.S.C. 154(b) by 0 days.

(21) Appl. No.: 09/245,228

(22) Filed: Feb. 5, 1999

(51) Int. Cl.$^7$ .................................. A61B 1/267

(52) U.S. Cl. .................. 600/185; 600/190; 600/197; 600/191

(58) Field of Search ................... 600/185, 190, 600/191, 192, 197, 199

(56) References Cited

U.S. PATENT DOCUMENTS

| | | | |
|---|---|---|---|
| 3,507,272 | * | 4/1970 | Laerdal ............................. 128/16 |
| 3,598,113 | * | 8/1971 | Moore et al. ..................... 128/11 |
| 3,766,909 | | 10/1973 | Ozbey . |
| 4,037,588 | | 7/1977 | Heckele . |
| 4,086,919 | | 5/1978 | Bullard . |
| 4,306,547 | | 12/1981 | Lowell . |
| 4,384,570 | | 5/1983 | Roberts . |
| 4,425,909 | * | 1/1984 | Rieser ............................... 128/16 |
| 4,437,458 | | 3/1984 | Upsher . |
| 4,570,614 | | 2/1986 | Bauman . |
| 4,669,449 | | 6/1987 | Bauman . |
| 4,679,547 | | 7/1987 | Bauman . |
| 4,694,822 | | 9/1987 | Bauman . |
| 4,729,367 | | 3/1988 | Bauman . |
| 4,815,451 | | 3/1989 | Bauman . |
| 4,834,077 | | 5/1989 | Sun . |
| 4,947,896 | | 8/1990 | Bartlett . |
| 4,982,729 | | 1/1991 | Wu . |
| 5,063,907 | | 11/1991 | Musicant et al. . |
| 5,070,859 | | 12/1991 | Waldvogel . |
| 5,178,131 | | 1/1993 | Upsher . |
| 5,178,132 | * | 1/1993 | Mahefky .............................. 128/17 |

(List continued on next page.)

OTHER PUBLICATIONS

Wu, "A New Laryngoscope: The Combination Intubating Device", Anesthesiology, vol. 81, No. 4, Oct. 1994, pp. 1085–1087.

"Bioblad", G. Bidoia Medical Products—Anaesthesia and Surgery, bihos.com/bidoia/anaesthesia.html, 1998.

BladeLightSource, blridge.com/bladelig.htm, 1998.

*Primary Examiner*—Lee Cohen
*Assistant Examiner*—Jocelyn Ram
(74) *Attorney, Agent, or Firm*—Edward W. Callan

(57) ABSTRACT

In a laryngoscope, a blade for displacing a person's tongue in order to facilitate insertion of an endotracheal tube into the person's trachea includes a distal portion for insertion through the person's mouth and into the person's oropharynx and an elongated portion extending from the distal portion; the elongated portion is substantially wider than the distal portion and includes an inner side that is disposed for contacting and displacing the person's tongue when the distal portion is inserted into the person's oropharynx; and the inner side of the elongated portion is laterally contoured for restraining the person's tongue in a relatively centered position while the tongue is being displaced. The blade and the handle of the laryngoscope are injection molded in the same mold and may be of the same plastic material. Preferably the blade is transparent for transmitting light from a light source in the handle. The transmitted light is emitted from the blade to illuminate the person's oropharynx when the distal portion is inserted into the person's oropharynx. The handle includes a portion that extends directly from the blade and is curved longitudinally so that the handle can be gripped at different angles with respect to the blade. Preferably, the blade also is curved longitudinally.

27 Claims, 4 Drawing Sheets

U.S. PATENT DOCUMENTS

| | | |
|---|---|---|
| 5,261,392 | 11/1993 | Wu . |
| 5,263,472 | 11/1993 | Ough . |
| 5,425,356 | 6/1995 | Ough . |
| 5,438,976 | 8/1995 | Nash . |
| 5,501,651 | 3/1996 | Bauman . |
| 5,529,570 | 6/1996 | Storz . |
| 5,536,245 | 7/1996 | Dahlbeck . |
| 5,542,905 | 8/1996 | Nussenbaum . |
| 5,575,758 * | 11/1996 | Easterbrook, III .................... 600/193 |
| 5,651,761 | 7/1997 | Upsher . |
| 5,702,351 * | 12/1997 | Bar-Or et al. ........................ 600/190 |
| 5,888,195 * | 3/1999 | Schneider ............................. 600/199 |
| 5,938,591 * | 8/1999 | Minson ................................ 600/191 |
| 5,984,863 * | 11/1999 | Ansari ................................. 600/185 |

* cited by examiner

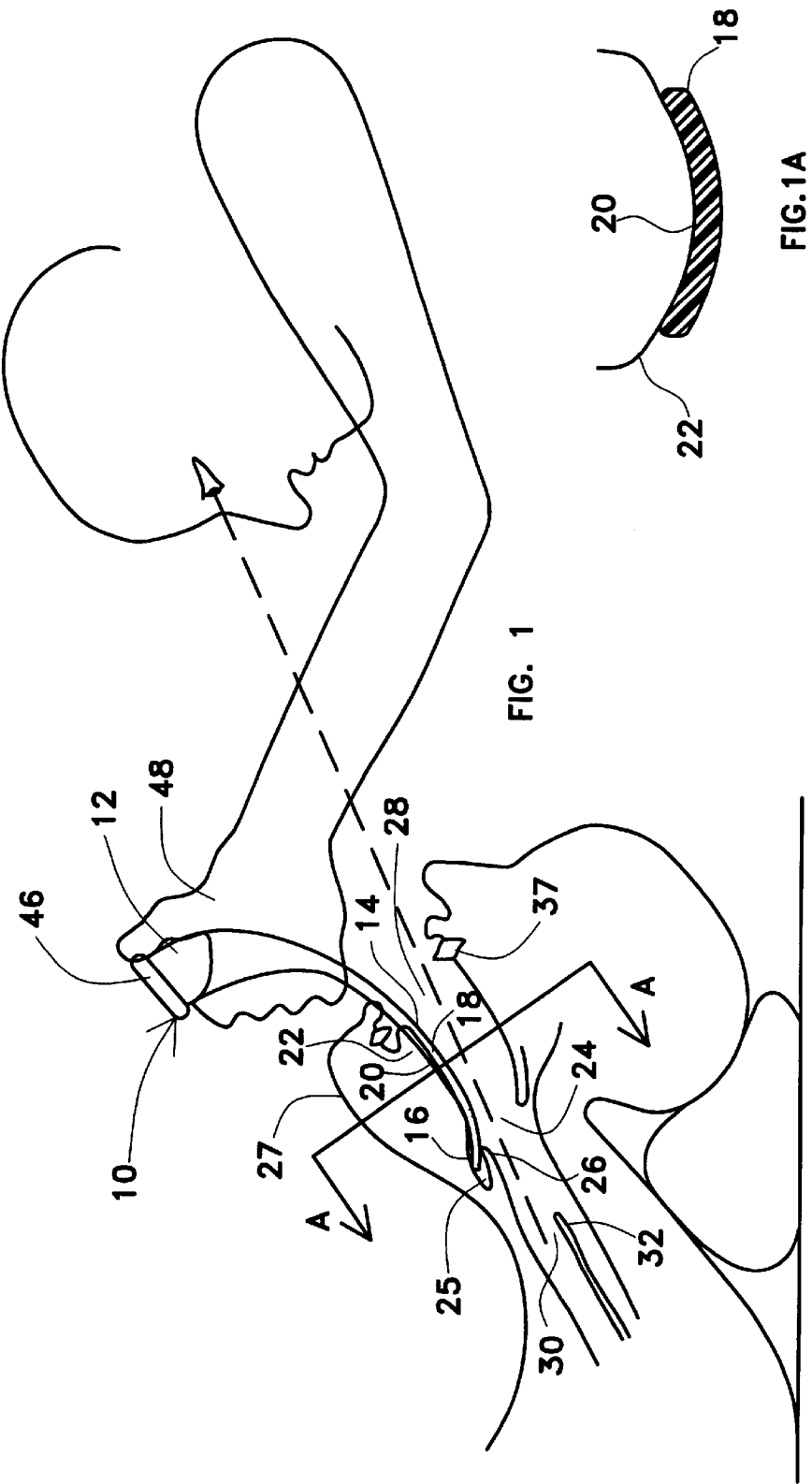

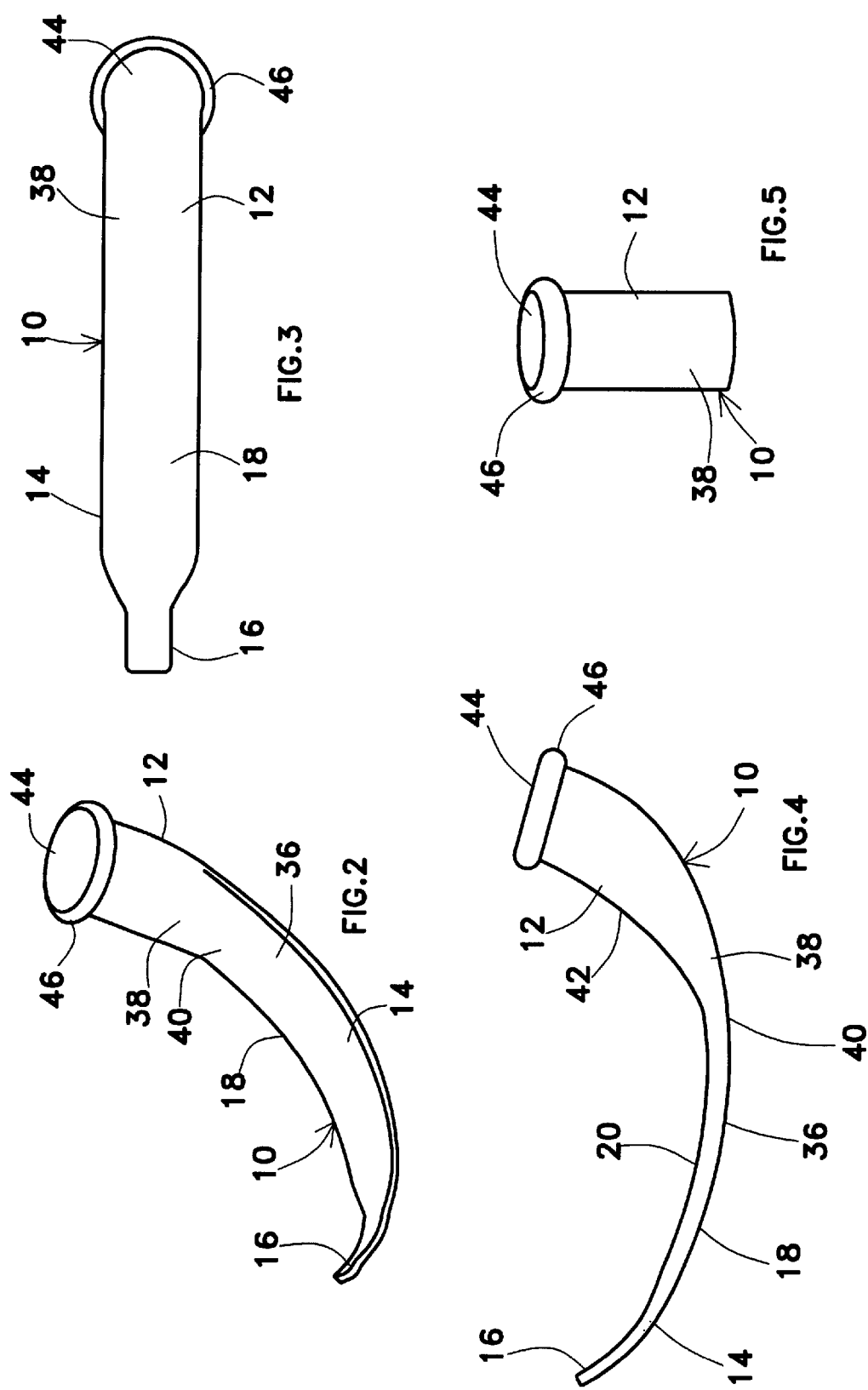

LARYNGOSCOPE

BACKGROUND OF THE INVENTION

The present invention generally pertains to laryngoscopes and is particularly directed to improvements thereto that ease the use thereof.

A laryngoscope is a device having a blade that is inserted into a person's mouth for the purpose of holding open the person's mouth while displacing the person's tongue in order to facilitate insertion of an endotracheal tube into the person's trachea. Typically, the blade includes a distal portion for insertion through the person's mouth and into the person's oropharynx; and an elongated portion extending from the distal portion; wherein the elongated portion is substantially wider than the distal portion and includes an inner side that is disposed for contacting and displacing the person's tongue when the distal portion is inserted into the person's oropharynx. Some blades are curved longitudinally to define a dorsal side and a curved inner side that includes the inner side of the elongated portion that contacts the tongue. A laryngoscope also includes a handle extending from the blade.

Prior art laryngoscopes are of complex construction. A light source is provided within some laryngoscopes for illuminating the oropharynx to enhance accurate insertion of both the laryngoscope blade and the endotracheal tube. Some laryngoscope blades are made of transparent plastic material for transmitting light from the light source toward the oropharynx. Other laryngoscopes include optical fibers within the blade for transmitting light from the light source toward the oropharynx. In other laryngoscopes, a light source for illuminating the oropharynx is contained within a superstructure on the opposite side of the blade from the side that contacts the tongue.

Prior art laryngoscopes are difficult to use because the tongue is slippery and tends to slide to one side or the other while the laryngoscope is being inserted and thereby partially obstructs the view of the oropharynx and access to the trachea, and because the typical handle is so contoured and disposed in relation to the blade that some persons have trouble gripping the laryngoscope in such a manner as to apply appropriate leverage for holding open the mouth while displacing the tongue.

SUMMARY OF THE INVENTION

In one aspect, the present invention provides a laryngoscope blade for displacing a person's tongue in order to facilitate insertion of an endotracheal tube into the person's trachea, comprising a distal portion for insertion through the person's mouth and into the person's oropharynx; and an elongated portion extending from the distal portion; wherein the elongated portion is substantially wider than the distal portion and includes an inner side that is disposed for contacting and displacing the person's tongue when the distal portion is inserted into the person's oropharynx; and wherein the inner side of the elongated portion is laterally contoured for restraining the person's tongue in a relatively centered position while the tongue is being displaced. In the preferred embodiment, the inner side of the elongated portion has a concave lateral contour for effecting said restraint of the person's tongue while the tongue is being displaced.

In another aspect, the present invention provides laryngoscope for holding open a person's mouth while displacing the person's tongue in order to facilitate insertion of an endotracheal tube into the person's trachea, comprising a blade for contacting and displacing the person's tongue when a distal portion of the blade is inserted into the person's oropharynx; and a unitary handle including a handle portion extending directly from the blade that is curved longitudinally so that the handle can be gripped at different angles with respect to the blade; wherein a dorsal side of the handle is defined by the curvature of the curved portion of the handle; wherein the blade includes a portion that is curved longitudinally to define a dorsal side of the blade; and wherein the dorsal side of the blade merges with the dorsal side of the handle in a region of continuous longitudinal curvature. Accordingly, one is able to grip the laryngoscope in an individualistic manner in order to better apply appropriate leverage for holding open the mouth while displacing the tongue.

In a further aspect, the present invention provides a laryngoscope for holding open a person's mouth while displacing the person's tongue in order to facilitate insertion of an endotracheal tube into the person's trachea, comprising a blade for contacting and displacing the person's tongue when a distal portion of the blade is inserted into the person's oropharynx; and a unitary handle including a handle portion extending directly from the blade that is curved longitudinally so that the handle can be gripped at different angles with respect to the blade; wherein a distal portion of the handle includes a protruding rim for inhibiting slippage of one's hand from the handle.

Additional features of the present invention are described with reference to the detailed description of the preferred embodiments.

BRIEF DESCRIPTION OF THE DRAWING

FIG. 1 illustrates the insertion of a laryngoscope according to the present invention into the mouth of a person.

FIG. 1A is a sectional view of the blade of the laryngoscope of FIG. 1 taken along lines A—A in FIG. 1.

FIG. 2 is a perspective view of a preferred embodiment of a laryngoscope according to the present invention.

FIG. 3 is a bottom view of the laryngoscope of FIG. 2.

FIG. 4 is a side view of the laryngoscope of FIG. 2.

FIG. 5 is an end view of the laryngoscope of FIG. 2.

DETAILED DESCRIPTION

Figure 6:
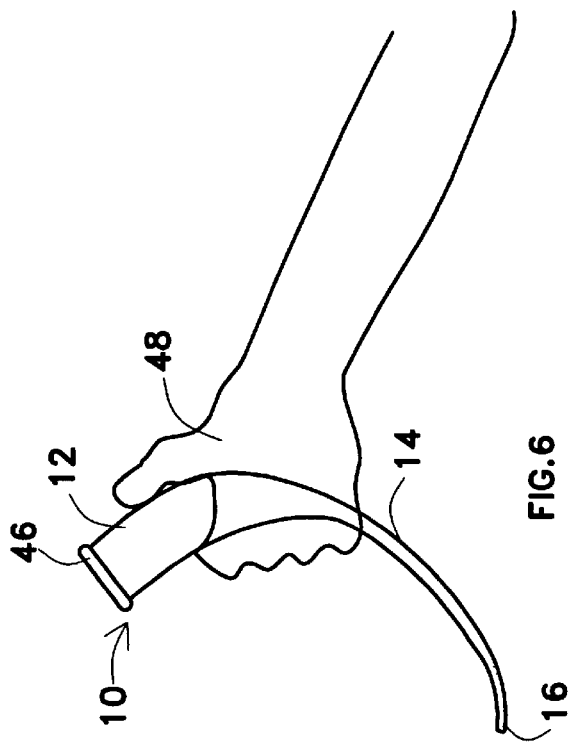
FIG. 6 illustrates the handle of the laryngoscope being gripped at a different location than as shown in FIG. 1.

Referring to FIGS. 1 through 5, a preferred embodiment of a laryngoscope 10 according to the present invention includes a handle 12 and a blade 14 extending from the handle 12. The blade 14 includes a distal portion 16 and an elongated portion 18 extending from the distal portion 16 to the handle 12. The elongated portion 18 is substantially wider than the distal portion 16 and includes an inner side 20 that is disposed for contacting and displacing the person's tongue 22 when the distal portion 16 is inserted into a person's oropharynx 24. The inner side 20 of the elongated portion 18 is laterally contoured for restraining the person's tongue 22 in a relatively centered position while the tongue 22 is being displaced. Preferably, the inner side 20 of the elongated portion 18 has a concave lateral contour, as shown in FIG. 1A, for effecting such restraint of the tongue 22 while the tongue 22 is being displaced.

Figure 1B:
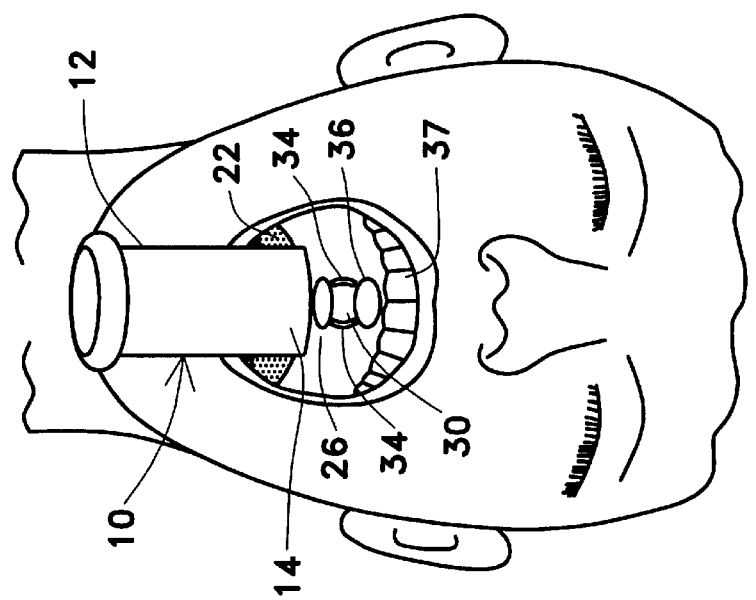
FIG. 1B is a view of the head of a person having the laryngoscope of FIG. 1 inserted into his mouth as seen by the person inserting the laryngoscope.

The distal portion 16 of the blade 14 is inserted into the vallecula 25 between the base of the tongue 22 and the epiglottis 26; and leverage is applied with the laryngoscope 10 to lift the jaw 27 in order to hold open the mouth 28 while displacing the tongue 22 and thereby provide a better view of the trachea 30 between the epiglottis 26, the esophagus wall 32 and the vocal cords 34, as shown in FIG. 1B.

Preferably, the blade 14 is curved longitudinally, as shown in FIG. 4, to define a dorsal side 36 and a curved inner side 20 that includes the inner side 20 of the elongated portion 18. Preferably, the dorsal side 36 of the blade 14 is devoid of superstructure that would obstruct visualization of the trachea 30 when the distal portion 16 of the blade 14 is inserted into the oropharynx 24. The absence of superstructure on the dorsal side 36 of the blade 14 also makes it less likely that the blade 14 will contact and possibly damage the upper teeth 37 of the person while the blade 14 is being inserted.

In some preferred embodiments, the handle 12 is a unitary handle 12 that extends directly from the blade 14, and the handle 12 includes a portion 38 that is curved longitudinally so that the handle 12 can be gripped at different angles with respect to the blade 14, as shown in FIGS. 1 and 6. A dorsal side 40 of the handle 12 is defined by the curvature of the curved portion 38 of the handle 12; and the dorsal side 36 of the blade 14 merges with the dorsal side 40 of the handle 12 in a region of continuous longitudinal curvature. The longitudinally curved portion 38 of the handle 12 further defines an inner side 42 of the handle 12 having a smooth inner profile.

In some preferred embodiments, a distal portion 44 of the handle 12 includes a protruding rim 46 for inhibiting slippage of one's hand 48 from the handle 12.

Figure 7:
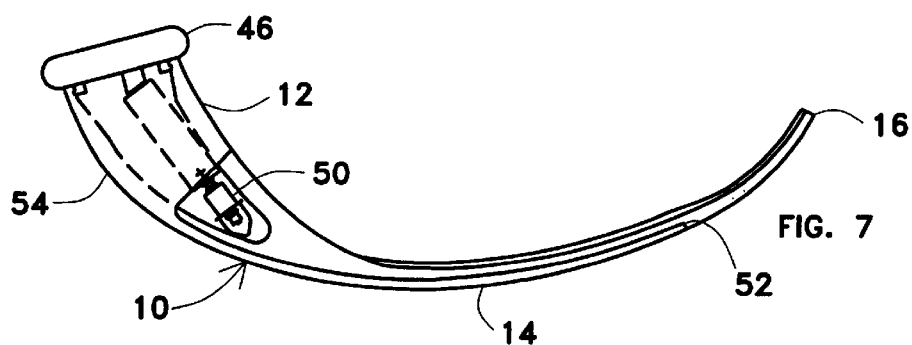
FIG. 7 illustrates the transparency and opacity characteristics of a preferred embodiment of the laryngoscope of FIGS. 1–5.

Referring to FIG. 7, a light source 50 is disposed in the handle 12. The blade 14 is a transparent material, preferably plastic, and thereby is light transmissive for emitting light transmitted through the blade 14 from the light source 50 to illuminate the oropharynx 24 when the distal portion 16 if the blade 14 is inserted into the person's oropharynx 24. A transparent plastic embodiment of the blade 14 has a predominantly smooth surface that was formed by at least one highly-polished section of a injection-molding mold part. The transparent plastic embodiment of the blade 14 also has a rough surface in a portion 52 of the blade 14 from which light is emitted. The rough surface was formed for the purpose of enabling light to be emitted therefrom by using at least one injection-molding mold-part section having a stone finish to define the portion 52 of the blade 14. Alternatively, the transparent plastic embodiment of the blade 14 has at least a portion of a Fresnel lens in the portion 52 of the blade 14 from which light is emitted. The light source 50 includes an on/off switch.

For one preferred embodiment of the laryngoscope of FIG. 7, the handle 12 and the blade 14 are injection molded in the same mold. Preferably, the handle 12 and the blade 14 are formed of a single transparent plastic material. It is also preferred that at least a portion 54 of the handle 12 is rendered opaque by a coating or cover of some sort so that light from the light source 50 does not shine directly into the eyes of a user of the laryngoscope while the blade 14 is being inserted into the oropharynx 24. The light source 50 can be removed from the handle 12 for reuse in another laryngoscope when the laryngoscope 10 is disposed of after a single use.

Alternatively, the handle 12 and the blade 14 of the laryngoscope of FIG. 7 are injection molded in the same mold, with an opaque portion 54 of the handle 12 and the blade 14 being formed by injection of an opaque plastic material and the remainder of the handle 12 and the blade 14 being formed by injection of transparent plastic material.

Figure 8:
FIG. 8 illustrates an alternative longitudinal contour of a laryngoscope according to the present invention.
Figure 9:
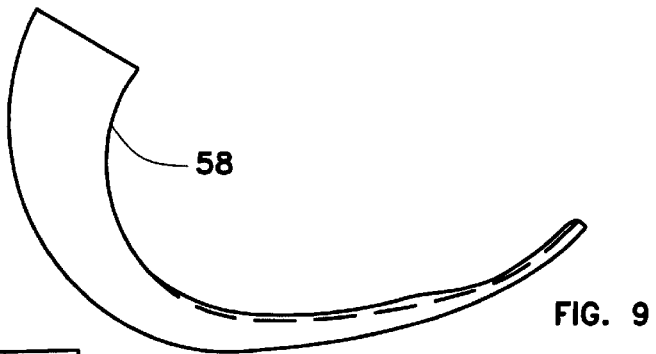
FIG. 9 illustrates another alternative longitudinal contour of a laryngoscope according to the present invention.

To accommodate insertion into different size mouths, there are provided laryngoscopes having blades of different dimensions and/or different degrees of longitudinal curvature, such as the respective laryngoscopes 56, 58 shown in FIGS. 8 and 9, which in other respects are the same as described above with reference to FIGS. 1–7.

Figure 10:
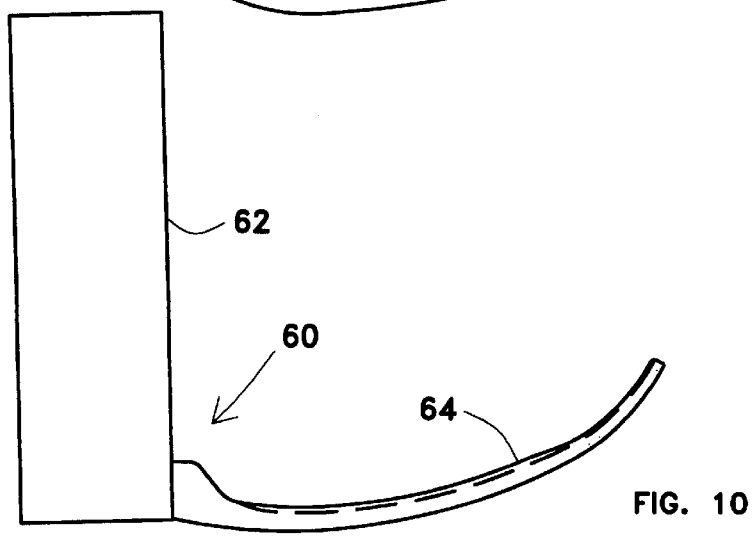
FIG. 10 illustrates an alternative embodiment of a laryngoscope according to the present invention.

In another preferred embodiment, as shown in FIG. 10, a laryngoscope 60 according to the present invention includes a handle 62 and a blade 64 that is detachable from the handle 62. The blade 64 is manufactured apart from the handle 62. The handle 62 includes a light source and at least a portion of the blade 64 is made of a transparent material for transmitting light from the light source to the oropharynx. The blade 64 includes the features of the blade 14 included in the laryngoscope 10 described above with reference to FIGS. 1–7. The handle 62 is reusable and the blade 64 is disposable. Detachable blades 64 having different degrees of curvature may be used with the handle 62. The handle 62 may be a prior art handle.

Alternative embodiments of laryngoscopes according to one or more aspect of the present invention do not necessarily include all of the features of the laryngoscope 10 described above with reference to FIGS. 1–7. For example, the blade does not have to be transparent, but rather may include optical fibers for transmitting light for illuminating the oropharynx upon insertion of the blade therein. Also, some superstructure may be included on the opposite side of the blade from the side thereof that contacts the tongue. In addition, the blade does not have to be curved longitudinally. In laryngoscopes according to those aspects of the invention wherein the handle and the blade are injection molded in the same mold, or wherein a portion of a unitary handle extending directly from the blade is curved longitudinally so that the handle can be gripped at different angles with respect to the blade, the inner side of the elongated portion does not have to be laterally contoured for restraining the person's tongue in a relatively centered position while the tongue is being displaced, although such a lateral contour is preferred.

The advantages specifically stated herein do not necessarily apply to every conceivable embodiment of the present invention. Further, such stated advantages of the present invention are only examples and should not be construed as the only advantages of the present invention. While the above description contains many specificities, these should not be construed as limitations on the scope of the present invention, but rather as examples of the preferred embodiments described herein. Other variations are possible and the scope of the present invention should be determined not by the embodiments described herein but rather by the claims and their legal equivalents.

We claim:

1. A laryngoscope blade for displacing a person's tongue in order to facilitate insertion of an endotracheal tube into the person's trachea, comprising
   a distal portion for insertion through the person's mouth and into the person's oropharynx; and
   an elongated portion extending from the distal portion;
   wherein the elongated portion is substantially wider than the distal portion and includes an inner side that is disposed for contacting and displacing the person's tongue when the distal portion is inserted into the person's oropharynx; and
   wherein the inner side of the elongated portion is laterally contoured for restraining the person's tongue in a relatively centered position while the tongue is being displaced.

2. A laryngoscope blade according to claim 1, wherein the inner side of the elongated portion has a concave lateral contour for effecting said restraint of the person's tongue while the tongue is being displaced.

3. A laryngoscope blade according to claim 1, wherein the blade is curved longitudinally to define a dorsal side and a curved inner side that includes the inner side of the elongated portion.

4. A laryngoscope blade according to claim 3, comprising light transmissive means disposed for emitting transmitted light to illuminate the person's oropharynx when the distal portion is inserted into the person's oropharynx.

5. A blade according to claim 4, wherein the blade is transparent and thereby constitutes the light transmissive means.

6. A laryngoscope blade according to claim 5, wherein the blade is transparent plastic having a predominantly smooth surface that was formed by at least one highly-polished section of a injection-molding mold part.

7. A laryngoscope blade according to claim 6, wherein the blade has a rough surface in a portion of the blade from which light is emitted, the rough surface having been formed by at least one injection-molding mold-part section having a stone finish.

8. A laryngoscope blade according to claim 5, wherein the blade is transparent plastic having a rough surface in a portion of the blade from which light is emitted, the rough surface having been formed by at least one injection-molding mold-part section having a stone finish.

9. A laryngoscope blade according to claim 5, wherein the blade is transparent plastic having at least a portion of a Fresnel lens in a portion of the blade from which light is emitted.

10. A laryngoscope blade according to claim 3, wherein the dorsal side of the blade is devoid of superstructure that would obstruct visualization of the trachea when the distal portion of the blade is inserted into the person's oropharynx.

11. A laryngoscope blade according to claim 1, comprising light transmissive means disposed for emitting transmitted light to illuminate the person's oropharynx when the distal portion is inserted into the person's oropharynx.

12. A laryngoscope blade according to claim 11, wherein the blade is transparent and thereby constitutes the light transmissive means.

13. A laryngoscope blade according to claim 12, wherein the blade is transparent plastic having a predominantly smooth surface that was formed by at least one highly-polished section of a injection-molding mold part.

14. A laryngoscope blade according to claim 13, wherein the blade has a rough surface in a portion of the blade from which light is emitted, the rough surface having been formed by at least one injection-molding mold-part section having a stone finish.

15. A laryngoscope blade according to claim 12, wherein the blade is transparent plastic having a rough surface in a portion of the blade from which light is emitted, the rough surface having been formed by at least one injection-molding mold-part section having a stone finish.

16. A laryngoscope blade according to claim 12, wherein the blade is transparent plastic having at least a portion of a Fresnel lens in a portion of the blade from which light is emitted.

17. A laryngoscope for holding open a person's mouth while displacing the person's tongue in order to facilitate insertion of an endotracheal tube into the person's trachea, comprising
   a handle; and
   a blade extending from the handle, wherein the blade includes
   a distal portion for insertion through the person's mouth and into the person's oropharynx; and
   an elongated portion extending from the distal portion to the handle;
   wherein the elongated portion is substantially wider than the distal portion and includes an inner side that is disposed for contacting and displacing the person's tongue when the distal portion is inserted into the person's oropharynx; and
   wherein the inner side of the elongated portion is laterally contoured for restraining the person's tongue in a relatively centered position while the tongue is being displaced.

18. A laryngoscope blade according to claim 17, wherein the inner side of the elongated portion has a concave lateral contour for effecting said restraint of the person's tongue while the tongue is being displaced.

19. A laryngoscope according to claim 17, wherein the handle and the blade are injection molded in the same mold.

20. A laryngoscope according to claim 19, wherein the handle and the blade are formed of a single plastic material.

21. A laryngoscope according to claim 20, wherein the plastic material is transparent.

22. A laryngoscope according to claim 20, wherein the blade is transparent.

23. A laryngoscope for holding open a person's mouth while displacing the person's tongue in order to facilitate insertion of an endotracheal tube into the person's trachea, comprising a blade for contacting and displacing the person's tongue when a distal portion of the blade is inserted into the person's oropharynx; and a unitary handle including a handle portion extending directly from the blade that is curved longitudinally so that the handle can be gripped at different angles with respect to the blade;

wherein a dorsal side of the handle is defined by the curvature of the curved portion of the handle;

wherein the blade includes a portion that is curved longitudinally to define a dorsal side of the blade; and wherein the dorsal side of the blade merges with the dorsal side of the handle in a region of continuous longitudinal curvature.

24. A laryngoscope according to claim 23, wherein the longitudinally curved portion of the handle further defines an inner side of the handle having a smooth inner profile.

25. A laryngoscope according to claim 23, wherein the handle and the blade are injection molded in the same mold.

26. A laryngoscope according to claim 25, wherein the handle and the blade are formed of a single plastic material.

27. A laryngoscope for holding open a person's mouth while displacing the person's tongue in order to facilitate insertion of an endotracheal tube into the person's trachea, comprising a blade for contacting and displacing the person's tongue when a distal portion of the blade is inserted into the person's oropharynx; and a unitary handle including a handle portion extending directly from the blade that is curved longitudinally so that the handle can be gripped at different angles with respect to the blade;

wherein a distal portion of the handle includes a protruding rim for inhibiting slippage of one's hand from the handle.

* * * * *